(12) United States Patent
Jones et al.

(10) Patent No.: US 8,883,508 B2
(45) Date of Patent: *Nov. 11, 2014

(54) METHOD AND APPARATUS FOR DETERMINING FORMATION FLUID COMPOSITION

(71) Applicant: Halliburton Energy Services, Inc., Houston, TX (US)

(72) Inventors: Christopher M. Jones, Houston, TX (US); Michael T. Pelletier, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/938,042

(22) Filed: Jul. 9, 2013

(65) Prior Publication Data

US 2013/0295677 A1  Nov. 7, 2013

Related U.S. Application Data

(63) Continuation of application No. 13/738,561, filed on Jan. 10, 2013, now Pat. No. 8,492,152, which is a continuation of application No. 12/920,231, filed as application No. PCT/US2008/013757 on Dec. 16, 2008, now Pat. No. 8,367,413.

(51) Int. Cl.
*G01N 33/24* (2006.01)
*G01N 30/00* (2006.01)
(Continued)

(52) U.S. Cl.
CPC .......... *G01N 33/24* (2013.01); *G01N 30/8686* (2013.01); *G01N 33/2823* (2013.01);
(Continued)

(58) Field of Classification Search
USPC ........ 73/19.02, 23.35–23.42, 152.03, 152.19, 73/152.23–152.24, 152.28, 152.42, 73/152.54–152.55; 422/68.1, 89; 436/28–30, 161
See application file for complete search history.

(56) References Cited

U.S. PATENT DOCUMENTS 2,902,111 A  9/1959  Henke et al.
3,301,040 A  1/1967  Levy et al.
(Continued)

FOREIGN PATENT DOCUMENTS

WO  WO-0173424 A1  10/2001
WO  WO-2008064402 A1  6/2008
(Continued)

OTHER PUBLICATIONS

Fuller, Edward, et al., "Diffusion of Halogenated Hydrocarbons in Helium", Journal of Physical Chemistry vol. 73 No. 11, (Nov. 1969), 7 pgs.

(Continued)

*Primary Examiner* — Arlen Soderquist
(74) *Attorney, Agent, or Firm* — Schwegman Lundberg & Woessner, P.A.; Benjamin Fite

(57) ABSTRACT

In some embodiments, apparatus and systems, as well as methods, may operate to draw a formation fluid sample into a sampling port included in a down hole tool, to vaporize some part of the fluid sample to substantially fill an injection port with a gas phase, to differentiate gas components in the gas phase to provide differentiated gas components along a concentration gradient, to detect the differentiated gas components, and to determine a fingerprint of the differentiated gas components. Other apparatus, systems, and methods are disclosed.

20 Claims, 5 Drawing Sheets

(51) Int. Cl.
  *G01N 33/28* (2006.01)
  *G01N 30/88* (2006.01)
  *G01N 30/86* (2006.01)
  *G01N 30/34* (2006.01)
  *G01N 30/12* (2006.01)

(52) U.S. Cl.
  CPC ............... *G01N 30/88* (2013.01); *G01N 30/34* (2013.01); *G01N 2030/8854* (2013.01); *G01N 2030/126* (2013.01)
  USPC .......... 436/28; 73/19.02; 73/23.35; 73/23.36; 73/23.37; 73/23.38; 73/23.39; 73/23.4; 73/23.41; 73/23.42; 73/152.03; 73/152.19; 73/152.23; 73/152.24; 73/152.28; 73/152.42; 73/152.54; 73/152.55; 422/68.1; 422/89; 436/29; 436/30; 436/161

(56) References Cited

U.S. PATENT DOCUMENTS

| | | | |
|---|---|---|---|
| 3,589,171 | A | 6/1971 | Haley |
| 3,619,986 | A | 11/1971 | Mormont et al. |
| 3,926,561 | A | 12/1975 | Lucero |
| 4,166,727 | A | 9/1979 | Pinto de Novais Paiva |
| 4,739,654 | A | 4/1988 | Pilkington et al. |
| 4,770,675 | A | 9/1988 | Kurzweg et al. |
| 4,976,750 | A | 12/1990 | Munari |
| 5,190,667 | A | 3/1993 | Jaeger |
| 5,304,494 | A | 4/1994 | Eisenmann |
| 5,351,532 | A | 10/1994 | Hager |
| 5,652,398 | A | 7/1997 | Johnson |
| 5,741,960 | A | 4/1998 | Payne et al. |
| 5,859,430 | A | 1/1999 | Mullins et al. |
| 6,063,166 | A | 5/2000 | Wilson |
| 6,074,461 | A | 6/2000 | Wilson |
| 6,137,010 | A | 10/2000 | Joo et al. |
| 6,175,409 | B1 | 1/2001 | Nielsen et al. |
| 6,686,079 | B2 | 2/2004 | Zhang et al. |
| 6,881,585 | B1 | 4/2005 | Potyrailo et al. |
| 7,099,778 | B2 | 8/2006 | Chien |
| 7,229,593 | B1 | 6/2007 | Ho |
| 7,718,434 | B2 | 5/2010 | Freed |
| 8,367,413 | B2 | 2/2013 | Jones et al. |
| 8,492,152 | B2 | 7/2013 | Jones et al. |
| 2002/0178785 | A1 | 12/2002 | Lo et al. |
| 2004/0045350 | A1 | 3/2004 | Jones et al. |
| 2004/0109156 | A1 | 6/2004 | DiFoggio et al. |
| 2004/0142386 | A1 | 7/2004 | Rigler et al. |
| 2004/0159149 | A1 | 8/2004 | Williams et al. |
| 2005/0178747 | A1 | 8/2005 | Shibamoto |
| 2005/0269499 | A1 | 12/2005 | Jones et al. |
| 2007/0125233 | A1 | 6/2007 | Bostrom et al. |
| 2007/0291265 | A1 | 12/2007 | Holman et al. |
| 2008/0121016 | A1 | 5/2008 | Shah et al. |
| 2008/0121017 | A1 | 5/2008 | Shah et al. |
| 2008/0141767 | A1 | 6/2008 | Raghuraman et al. |
| 2011/0023583 | A1 | 2/2011 | Jones et al. |
| 2011/0023594 | A1 | 2/2011 | Pelletier et al. |
| 2013/0122595 | A1 | 5/2013 | Jones et al. |

FOREIGN PATENT DOCUMENTS

| | | |
|---|---|---|
| WO | WO-2008067296 A2 | 6/2008 |
| WO | WO-2010071619 A1 | 6/2010 |

OTHER PUBLICATIONS

Canadian Application Serial No. 2,717,892, Office Action mailed Dec. 3, 2013, 3 pgs.

European Application Serial No. 08876377.6, Office Action mailed Jul. 25, 2011, 2 pgs.

European Application Serial No. 08876377.6, Response filed Dec. 11, 2012 to Office Action mailed Jun. 18, 2012, 11 pgs.

European Application Serial No. 13181785.0, Extended European Search Report mailed Oct. 22, 2013, 7 pgs.

European Application Serial No. 13181785.0, Examination Notification Art. 94(3) mailed Jul. 3, 2014, 3 pgs.

METHOD AND APPARATUS FOR DETERMINING FORMATION FLUID COMPOSITION

This application is a continuation application of U.S. patent application Ser. No. 13/738,561, filed on Jan. 10, 2013, now issued as U.S. Pat. No. 8,492,152, which application is a continuation application of U.S. patent application Ser. No. 12/920,231, filed on Sep. 30, 2010, now issued as U.S. Pat. No. 8,367,413, which application is a U.S. National Stage Filing under 35 U.S.C. 371 from International Patent Application Serial No. PCT/US2008/013757, filed Dec. 16, 2008, and published on Jun. 24, 2010 as WO 2010/071619 A1, the contents of which are incorporated herein by reference in their entirety.

BACKGROUND INFORMATION

Fluids (e.g., oil, water, and gas) exist in a variety of materials, including geological formations. These fluids are often recovered using a well, or a borehole cut into a formation. During exploration and recovery operations, it is sometimes useful to determine the characteristics of formation fluid chemistry in real time, such as the gas-to-oil ratio (GOR).

Compositional analysis of fluids down hole can be performed using optical spectroscopy. Although such methods are explicate for some components such as methane, the results are only approximate for light end fractions, and interpretative for contamination, all such results are highly matrix dependent. That is, pressure-volume-temperature (PVT) derived properties such as the GOR are correlated, and not directly measured. A molecular weight distribution of a sample is one compositional determination that may be performed.

Other available methods to determine molecular weight include osmosis, freezing point depression, and mass spectrometry. Of these methods, only mass spectrometry, which involves delicate and expensive instrumentation, yields a molecular weight distribution without prior separation.

DETAILED DESCRIPTION

In some embodiments, the challenges described above may be addressed by using gas diffusion to make a determination of molecular weight. A molecular weight distribution sensor that makes use of gas diffusion in the down hole environment may comprise a number of components, including one or more of the following:
Sampling Port
Carrier/Buffer Gas Reservoir
Vaporization Section
Injection Port
Diffusion Section
Detection Section (comprising one or more detectors)
Vacuum Section
Reaction Section
Desiccant Section
Data acquisition and calculation component The sections may be assembled in a number of ways to achieve the desired result. Thus, even though only a few embodiments are described herein for the sake of simplicity, so as not to obscure the operations described, it should be noted that a number of variations in the structure shown are possible. For instance the detection section may be located on either side of the reaction section and thereby incorporated into the vacuum section. It should also be noted that the use of the term "vacuum section" does not imply any particular absolute pressure—only a negative concentration gradient. A brief description of the apparatus operation follows, after which a more detailed explanation of the individual components and their function is given.

In use, the assembled apparatus may operate to draw fluid into the sampling port for injection into the vaporization section, to substantially fill the injection port with a quantity of the fluid converted to the gas phase. The injection section is connected to the diffusion section whereby differentiation of the gas components occurs along a concentration gradient. The rate of differentiation depends on the molecular mass of the gas components, among other parameters.

The temporally differentiated gas is detected and then transmitted to a vacuum concentration of lower pressure for disposal. Data received from the detection section, comprising one or more detectors, is used to determine the molecular weight distribution of gas phase components.

In some embodiments, no carrier/buffer gas is included, and no distinction between the injection port and diffusion section is made. Also no specification as to the vacuum section mechanism is made. Under these circumstances, molecular weight determination is possible, however the mathematical inversion from detector output to molecular weight distribution is relatively complex. Thus, some embodiments make use of the inversion process in combination with a working vacuum process conducted under down hole conditions. A more detailed explanation of the individual components and their function now follows.

Apparatus

Figure 1:
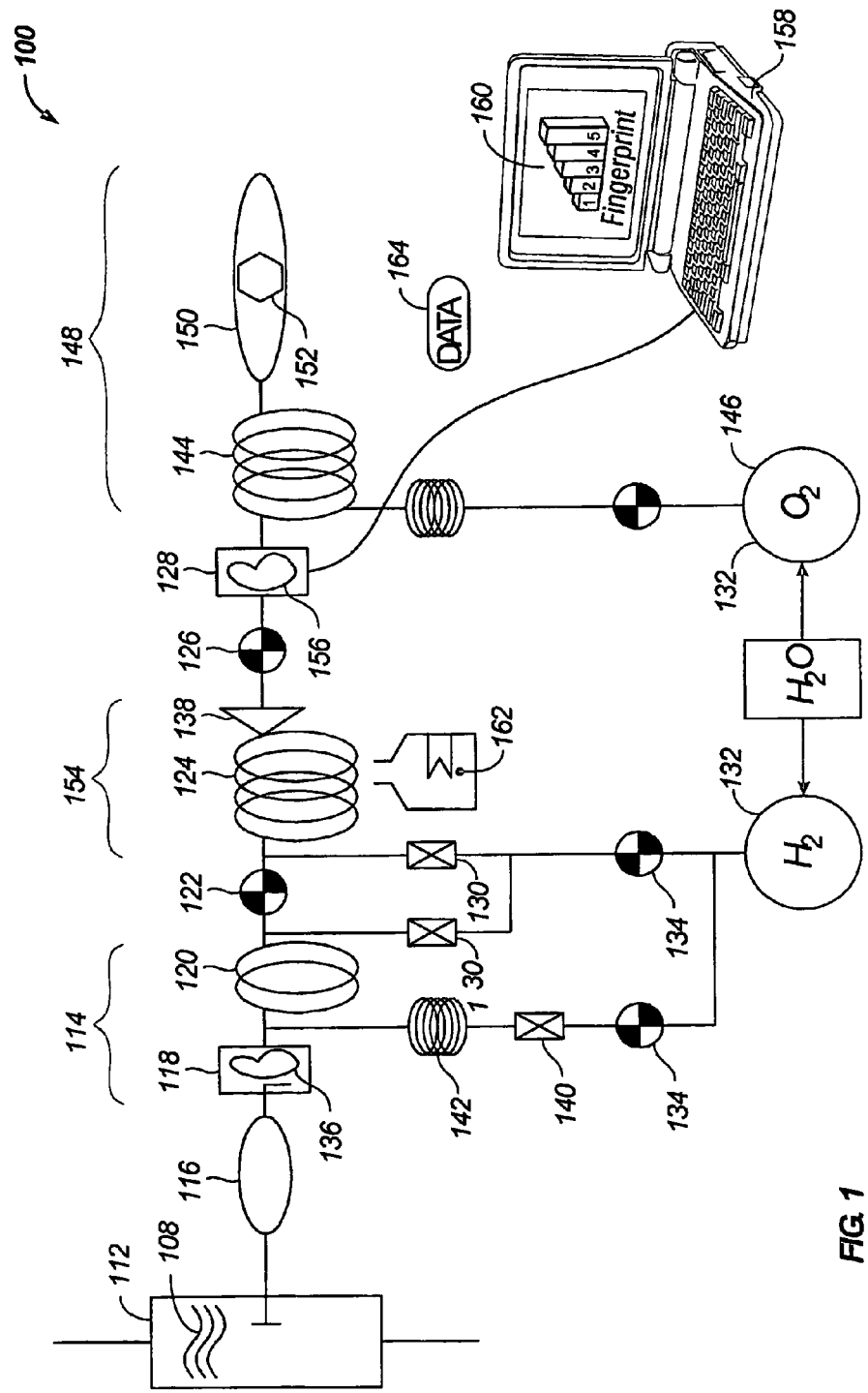
FIG. 1 is a block diagram of a formation fluid composition determination apparatus according to various embodiments of the invention.

FIG. 1 is a block diagram of a formation fluid composition determination apparatus 100 according to various embodiments of the invention. To begin operations, a known volume of fluid 108 is taken from a sampling port 112, perhaps comprising a single-phase sampler, and injected into the vaporization section 114. The sampling port 112 may employ trapped density driven segregation to provide a single oil, water, or gas phase with or without phase detection, providing a substantially homogenous sample.

The volume of the fluid 108 sampled should be sufficiently small to prevent overwhelming the vacuum system, and sufficiently large to gain a statistically representative sample that is then injected into a vaporization section 118. In some embodiments, this amount is about ten micro-liters.

The injection process may include passing the fluid 108 through a flash valve 116 into a vaporization section 118, and on into an injection port 120. The vaporization section 114 should be sufficiently hot, and be provided with sufficient heat flow to vaporize components of the fluid 108 up to a desired component range without volatizing heavier components, such as asphaltenes, leading to buildup in the injection port 120 and diffusion section 124. The vaporization section 114 should be a lower temperature than the injection port 120 and the diffusion section 124 to reduce the likelihood of condensation in subsequent sections.

A barrier 122 between the injection port 120 and a diffusion section 124, such as a timed valve, may be provided. An additional barrier 126, such as another timed valve, may be located between the diffusion section 124 and the detection section 128.

A buffer gas (e.g., hydrogen) under pressure can be injected into both the diffusion section 124 and the inlet section of the diffusion section (e.g., at the outlet of the injection port 120) to obtain substantially equal pressure on both sides of the barrier 122. This pressure equilibrium may be achieved with check valves 130 located between the respective injection port 120 and diffusion 124 sections and the carrier/buffer gas reservoir 132. These check valves 130 may be isolated by barriers 134 (e.g., valves) once substantial pressure equilibrium is obtained. The buffer gas pressure should be sufficient to obtain a diluted gas phase fluid that promotes effective diffusion of individual gas components. This diffusion then depends on the buffer gas mass interaction with individual sample components, and not the complex mixture molecular mass, simplifying mathematical inversion of detector response to a particular molecular weight distribution. Pressure balancing is useful to prevent mass transport due to a pressure gradient that can occur after opening the barrier 122 between the injection port 120 and diffusion section 124.

Continuing the description of operations, the barrier 122 between the injection port 120 and diffusion section 124 is opened. The diffusion section 124 may comprise a non-reactive coiled tube of sufficient diameter to prevent thin film condensation segregation along the length of the tube. Condensation segregation is not desirable in this case due to the complexity to the resulting mathematical inversion process. However, in some embodiments, this type of condensation effect may be included as part of the inversion process. The diffusion section 124 may also comprise other elements, such as a membrane, or any other component that permits diffusion through the apparatus 100 as a function of molecular weight.

It is useful to maintain the injection port 120 and diffusion section 124 at substantially the same temperature, which is higher than the temperature of the vaporization section 118, in order to prevent condensation in any of these sections. It may also be useful to construct the injection port 120 and the diffusion section 124 so that they have a substantially similar diameter, preventing a concentration gradient from arising between the two sections.

After waiting a sufficient time for gas diffusion to occur along the length of the diffusion section 124, but not so long as to meet the boundary condition at the distal end of the diffusion section 124 where the barrier 126 is located, the barrier 126 is opened between the diffusion section 124 and detector 128.

In most embodiments, when the barrier 126 is first opened, only the buffer gas flows across the detector 128 as a baseline. As gas 136 flows out of the diffusion section 124 and across the detector 128, the response of the detector 128 changes as a function of the gas composition.

The detector 128 may comprise one or more thermal conductivity detectors (TCDs). Other detector systems can be used, in conjunction with the TCDs, or separately, such as flame ionization detectors (FIDs), and/or chip-based mass spectrometers, or optical detectors.

As the gas 136 flows out of the diffusion section 124, the pressure in the diffusion section 124 may drop. This increases the mean free path of molecules in the diffusion section 124 and speeds up diffusion, which can be desirable because heavy components diffuse more slowly than light components. Thus, as the pressure drops, the speed of differentiation for heavier components increases, which in turn increases temporal resolution for the differentiated components 156.

In some embodiments, a nozzle 138 may be placed at the distal end of the diffusion section 124. The nozzle 138 can be used to direct and concentrate the flow from the diffusion section 124 over the detector 128. It provides an orifice with a pressure differential to prevent back diffusion of gas from the detector section 128. It can also serve to reduce the pressure gradient and mass transport along the injection port 120 and diffusion section 124. In some cases, Gram's law of effusion may be used to bring about a secondary separation based on molecular mass at the orifice point.

After the pressure in the diffusion section 124 drops to a predetermined level, a valve 140, such as a check valve at the proximal end of the injection port 120 can be actuated to allow flow between the carrier/buffer gas reservoir 132 and the injection port 120/diffusion section 124. The valve 140 can be actuated automatically by the pressure differential.

The carrier gas can be used to flush the diffusion section 124, removing hydrocarbons that remain. This provides a quantitative mass balance, and prepares the apparatus 100 for another operational sequence.

One or more capillary tubes 142 (e.g., a capillary tube bundle) can be used to maintain a substantially steady volumetric flow of gas from the carrier/buffer gas reservoir 132 to the injection port 120 and the diffusion section 124, since the capacity of an ideal capillary tube is limited by its diameter, and not the pressure differential (when a sufficient pressure differential exists) at constant temperature. The capillary tubes 142 may also serve to reduce abrupt changes in pressure across the valve 140, including pressure pulsing or oscillations.

From the detector section 128, the differentiated components 156 of the gas pass into a reaction section 144, which may comprise a heated tube containing CuO or some other reactant catalyst. In the reaction section, hydrocarbons are converted to water and carbon dioxide, or some other appropriate product.

When hydrogen is used as a carrier gas, it may be converted in the reaction section 144 to water. Hydrogen may be produced by the electrolysis of deionized water with the byproduct oxygen. Oxygen 146, in turn, may be injected into the reaction section 144 to directly consume the hydrogen without consuming CuO, or injected into the vaporization section 114 and then ignited to both clean higher molecular weight components and prepare them for direct quantification and emission analysis. In addition, the heavy fraction may be speciated into nitrogen, carbon, oxygen, hydrogen, and sulfur components with additional detection. Since the chamber is cleaned prior to each use, spectroscopy on the heavy fraction may be performed. This process may include fluorescent spectroscopy.

From the reaction section 144, the components 156 of the gas can pass into the vacuum section 148, perhaps comprising a desiccant section 150 which absorbs some or all products of the reaction section 144. BaO may be used as the desiccant 152. However, other desiccant or desiccant systems may be used. In some embodiments, the reaction section 144 may not be present, since some desiccants directly adsorb organics. Potential dessicants 152 include oxides of aluminum, barium, calcium, or magnesium; magnesium perchlorate; sulfates of calcium, copper, magnesium, or sodium; boric anhydride; lithium aluminum hydride; phosphoric acid; phosphorous pentoxide; potassium carbonate; hydroxides of potassium or sodium; silica gel; sulfuric acid; and zinc chloride; among others.

After sufficient time has passed to allow all hydrocarbons to be flushed from the diffusion section 124, and a second (hydrogen only) baseline is obtained, the barriers 122, 126 can be reinitialized for another operational sequence. Any heating desired for the various sections may be implemented in a number of ways, including using heaters 162 that operate via electric current resistive heating. In some embodiments, the diffusion section 124 may comprise a chromatographic column. In this case, components of the fluid 108 are discretely separated, and detection can take place using any of the mechanisms described previously.

Data 164 acquired from the detector(s) 128 may be processed by a data acquisition and calculation component 158, such as an embedded processor, a digital signal processor, or some other computing device that is able to acquire the data 164 and invert it. Inversion by classical least squares (CLS), inverse least squares (ILS), singular value decomposition (SVD), principal component regression (PCR) and multivariate curve resolution (MCR) can be used. Other inversion techniques, such as time evolved factor analysis, or trilinear decomposition (if multiple detection techniques are employed) may also be used to provide a fingerprint 160. Thus, many embodiments may be realized.

For example, an apparatus 100 to determine formation fluid composition may comprise a sampling port 112 to admit a sample of formation fluid 108, and a vaporization section 114 to convert some part of the formation fluid 108 sample into a gas phase 136. The apparatus 100 may further comprise a receiving section 154 including at least one of a diffusion section 124, a separation section, or a differentiation section (e.g., a chromatographic column) to receive the gas phase from an injection port 120 coupled to the vaporization section 114, and to provide differentiated gas components 156 along a concentration gradient.

The diffusion section 124 may comprise a substantially non-reactive coiled tube. The separation section and differentiation section are not shown in FIG. 1, but can be visualized as taking the place of, or being added in line with the diffusion section 124.

The apparatus 100 may also comprise one or more detectors 128 to provide data 164 associated with the differentiated gas components 156, wherein the data 164 is used to determine a fingerprint 160 of the differentiated gas components. A "fingerprint" as used herein means a substantially unique set of characteristics provided by one or more analysis techniques that identifies a sample, such as the molecular weight distribution of one or more gas components 156 in a fluid sample 108, or in a gas phase 138 of the fluid sample 108.

The detectors 128 may comprise one or more of a TCD, an FID, and/or a photometric detector. A nozzle 138 may be used to couple the diffusion section 124 to the detectors 128, providing an orifice with a pressure differential to prevent back diffusion of gas through the detectors 128.

In various embodiments, the apparatus 100 may comprise a first controllable barrier 122 between the injection port 120 and the receiving section 154, and a second controllable barrier 126 between the receiving section 154 and the detector 128. The controllable barriers 122, 126 may comprise check valves, or other types of valves.

In many embodiments, the apparatus 100 comprises a vacuum section 148 to receive the differentiated gas components 156. The vacuum section 148 may comprise a reaction section 144 coupled to a desiccant section 150.

Heaters 162 may be used in various parts of the apparatus 100, including the diffusion section 124. Thus, in some embodiments, the apparatus 100 may comprise a heater 162 to heat the diffusion section 124.

In many embodiments, the apparatus 100 comprises at least one gas reservoir 132 to couple to the receiving section 154, the vaporization section 114, or both. For example, one of the reservoirs 132 may be coupled to the receiving section 154 if it exists, and to the vaporization section 114 if it does not, such as when a chromatographic column is used in place of the diffusion section 124.

Systems

Figure 2:
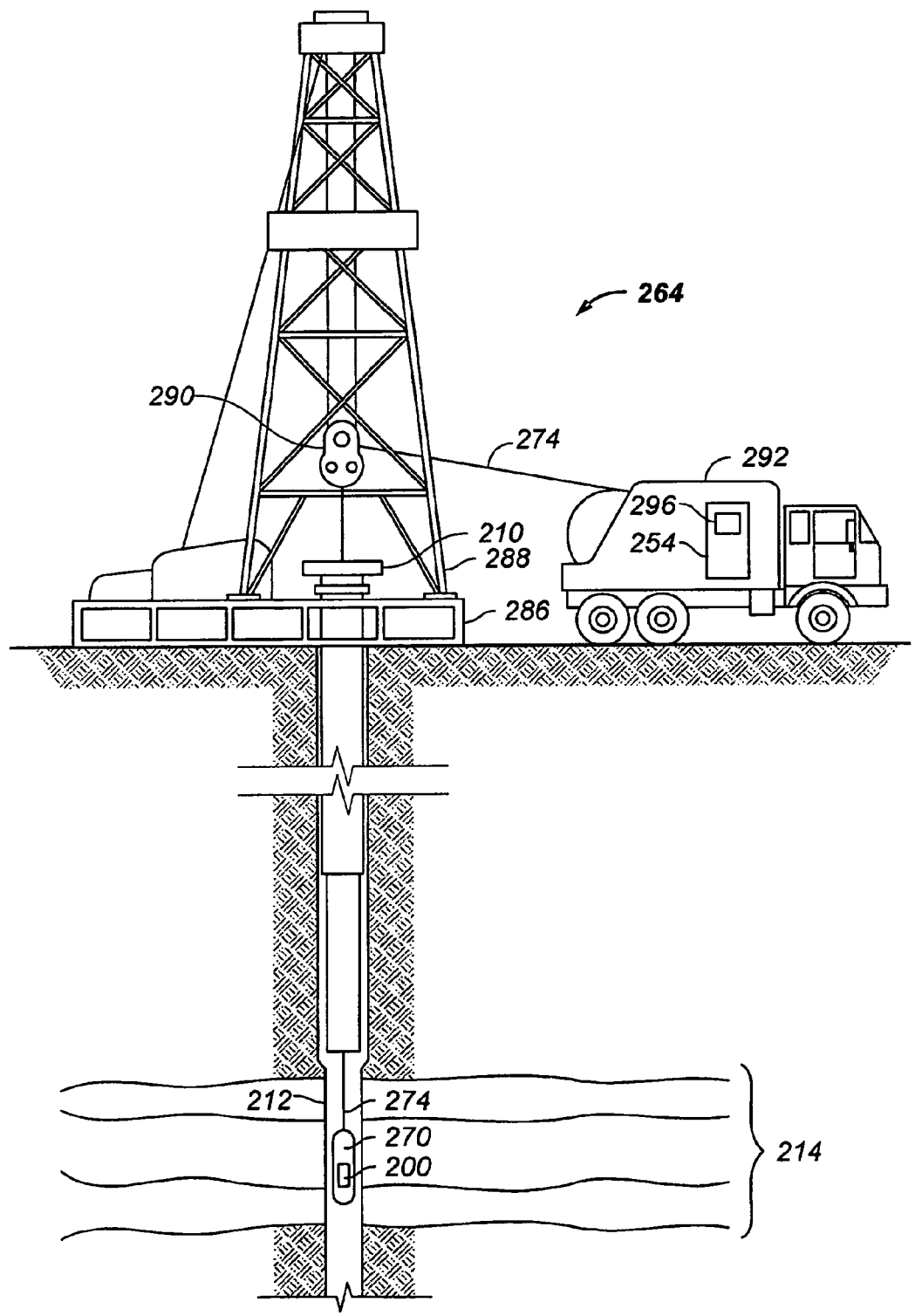
FIG. 2 is block diagram of apparatus and systems including a wireline implementation according to embodiments of the invention.
Figure 3:
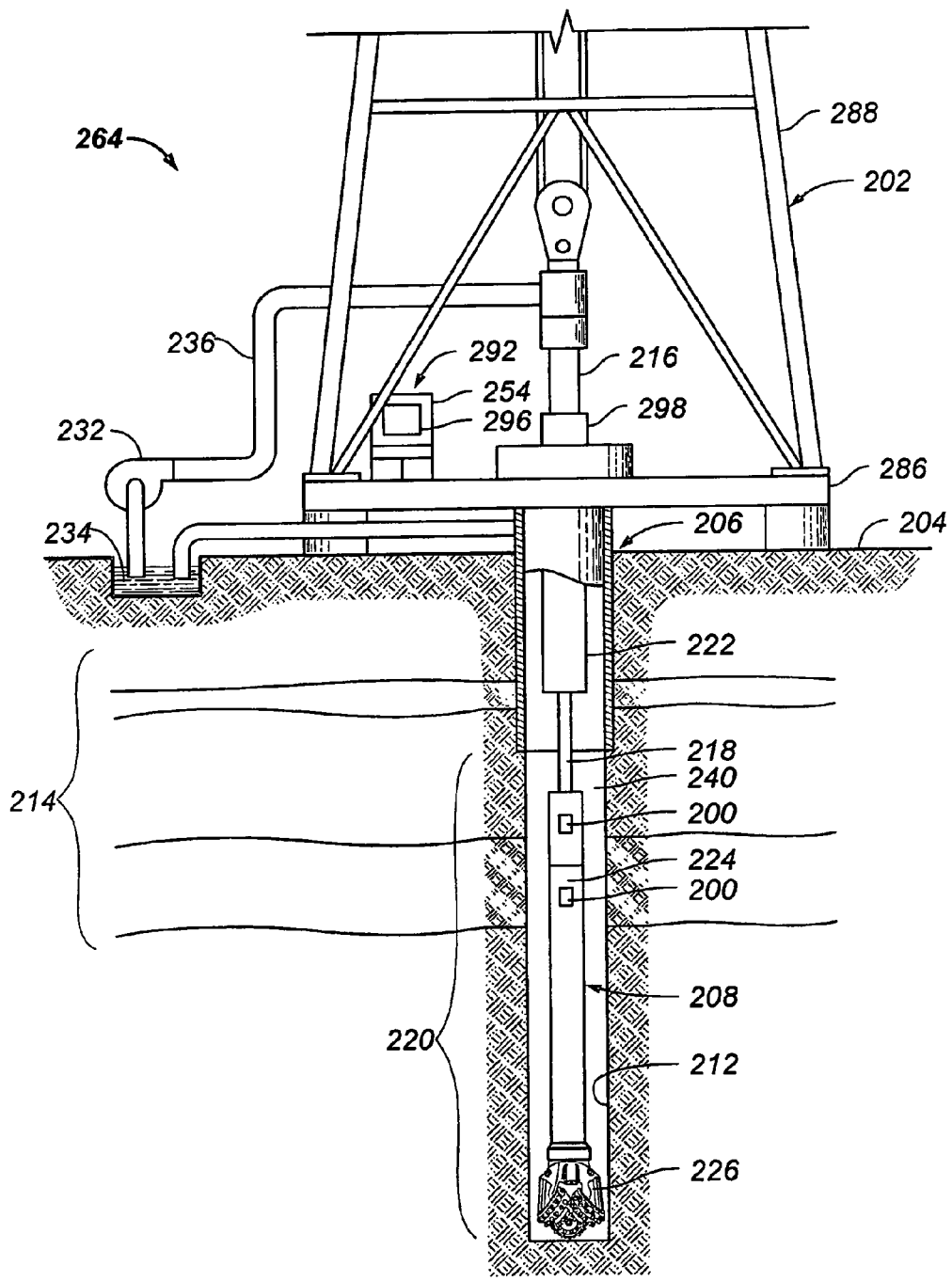
FIG. 3 is a block diagram of apparatus and systems including a drilling rig implementation according to various embodiments of the invention.

FIG. 2 is block diagram of apparatus 200 and systems 264 including a wireline implementation according to embodiments of the invention. FIG. 3 is a block diagram of apparatus 200 and systems 264 including a drilling rig implementation according to various embodiments of the invention. The apparatus 200, which may be similar to or identical to the apparatus 100 described above and shown in FIG. 1, may form portions of a tool body 270 as part of a wireline logging operation, or of a down hole tool 224 as part of a down hole drilling operation. A system 264 may comprise more than one of the apparatus 200.

Turning now to FIG. 2, a well as it appears during wireline logging operations can be seen. A drilling platform 286 may be equipped with a derrick 288 that supports a hoist 290. Oil and gas well drilling operations are commonly carried out using a string of drill pipes connected together so as to form a drilling string that is lowered through a rotary table 210 into a wellbore or borehole 212.

Here it is assumed that the drilling string has been temporarily removed from the borehole 212 to allow a tool body 270 (e.g., a wireline logging tool), such as a probe or sonde, to be lowered by wireline or logging cable 274 into the borehole 212. Typically, the tool body 270 is lowered to the bottom of the region of interest and subsequently pulled upward at a substantially constant speed. During the upward trip, instruments included in the tool body 270 (e.g., apparatus 200) may be used to perform measurements on the subsurface formations 214 adjacent the borehole 212 as they pass by, or as the tool body 270 remains stationary.

Measurement data (e.g., similar or identical to data 164 of FIG. 1) may include fluid sample fingerprint information and other data that can be communicated to a logging facility 292 for storage, processing, and analysis. The logging facility 292 may be provided with electronic equipment for various types of signal processing. Similar log data may be gathered and analyzed during drilling operations (e.g., during logging while drilling (LWD) operations). For example, the tool body 270 in this case may house one or more apparatus 200, and the logging facility 292 may include one or more surface computers 254, similar to or identical to the data acquisition and calculation component 158 described with respect to FIG. 1.

Turning now to FIG. 3, it can be seen how a system 264 may also form a portion of a drilling rig 202 located at a surface 204 of a well 206. The drilling rig 202 may provide support for a drill string 208. The drill string 208 may operate to penetrate a rotary table 210 for drilling a borehole 212 through subsurface formations 214. The drill string 208 may include a Kelly 216, drill pipe 218, and a bottom hole assembly 220, perhaps located at the lower portion of the drill pipe 218. The drill string 208 may include wired and unwired drill pipe, as well as wired and unwired coiled tubing, including segmented drilling pipe, casing, and coiled tubing.

The bottom hole assembly 220 may include drill collars 222, a down hole tool 224, and a drill bit 226. The drill bit 226 may operate to create a borehole 212 by penetrating the surface 204 and subsurface formations 214. The down hole tool 224 may comprise any of a number of different types of tools including measurement while drilling (MWD) tools, LWD tools, and others.

During drilling operations, the drill string 208 (perhaps including the Kelly 216, the drill pipe 218, and the bottom hole assembly 220) may be rotated by the rotary table 210. In addition to, or alternatively, the bottom hole assembly 220 may also be rotated by a top drive or a motor (e.g., a mud motor) that is located down hole. The drill collars 222 may be used to add weight to the drill bit 226. The drill collars 222 also may stiffen the bottom hole assembly 220 to allow the bottom hole assembly 220 to transfer the added weight to the drill bit 226, and in turn, assist the drill bit 226 in penetrating the surface 204 and subsurface formations 214.

During drilling operations, a mud pump 232 may pump drilling fluid (sometimes known by those of ordinary skill in the art as "drilling mud" or simply "mud") from a mud pit 234 through a hose 236 into the drill pipe 218 and down to the drill bit 226. The drilling fluid can flow out from the drill bit 226 and be returned to the surface 204 through an annular area 240 between the drill pipe 218 and the sides of the borehole 212. The drilling fluid may then be returned to the mud pit 234, where such fluid is filtered. In some embodiments, the drilling fluid can be used to cool the drill bit 226, as well as to provide lubrication for the drill bit 226 during drilling operations. Additionally, the drilling fluid may be used to remove subsurface formation 214 cuttings created by operating the drill bit 226.

Thus, referring now to FIGS. 1-3, it may be seen that in some embodiments, the system 264 may include a drill collar 222, and/or a down hole tool 224, or a tool body 270 or a substantially permanently installed probe (in a down hole well), to which one or more apparatus 200 are attached. The down hole tool 224 may comprise a wireline tool, an LWD tool, or MWD tool. The tool body 270 may comprise a wireline logging tool, including a probe or sonde, for example, coupled to a cable 274, such as a wireline or logging cable. Thus, a wireline 274 or a drill string 208 may be mechanically coupled to the down hole tool 224.

The down hole tool 224 may be used to at least partially house one or more apparatus 200, and in most embodiments is at least coupled to the apparatus 200 to obtain and provide a formation fluid sample to the apparatus 200. One or more displays 296 may be included in the system 264 as part of a surface computer 254 to display any type of acquired data and/or calculated formation fluid characteristic, including the GOR of the sampled formation fluid.

The apparatus 100, 200; fluid 108; sampling port 112; vaporization section 114; flash valve 116; vaporization section 118; injection port 120; barriers 122, 126, 134; diffusion section 124; detection section 128; valves 130, 140; gas reservoirs 132; gas 136; nozzle 138; capillary tubes 142; reaction section 144; vacuum section 148; desiccant section 150; desiccant 152; receiving section 154; differentiated components 156; data acquisition and calculation component 158; fingerprint 160; heaters 162; data 164; drilling rig 202; drill string 208; rotary table 210; Kelly 216, drill pipe 218; bottom hole assembly 220; drill collars 222; drill bit 226; mud pump 232; systems 264; tool body 270; logging cable 274; drilling platform 286; derrick 288; hoist 290; and logging facility 292 may all be characterized as "modules" herein. Such modules may include hardware circuitry, one or more processors and/or memory circuits, software program modules and objects, and firmware, and combinations thereof, as desired by the architect of the apparatus 100, 200 and systems 264, and as appropriate for particular implementations of various embodiments. For example, in some embodiments, such modules may be included in an apparatus and/or system operation simulation package, such as a software electrical signal simulation package, a power usage and distribution simulation package, a power/heat dissipation simulation package, and/or a combination of software and hardware used to simulate the operation of various potential embodiments.

It should also be understood that the apparatus and systems of various embodiments can be used in applications other than for borehole drilling and logging operations, and thus, various embodiments are not to be so limited. The illustrations of apparatus 100, 200 and systems 264 are intended to provide a general understanding of the structure of various embodiments, and they are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, embedded processors, and application-specific modules, including multilayer, multi-chip modules. Such apparatus and systems may further be included as subcomponents within a variety of electronic systems, such as process measurement instruments, personal computers, workstations, medical devices, and vehicles, among others. Some embodiments include a number of methods.

Methods

Figure 4:
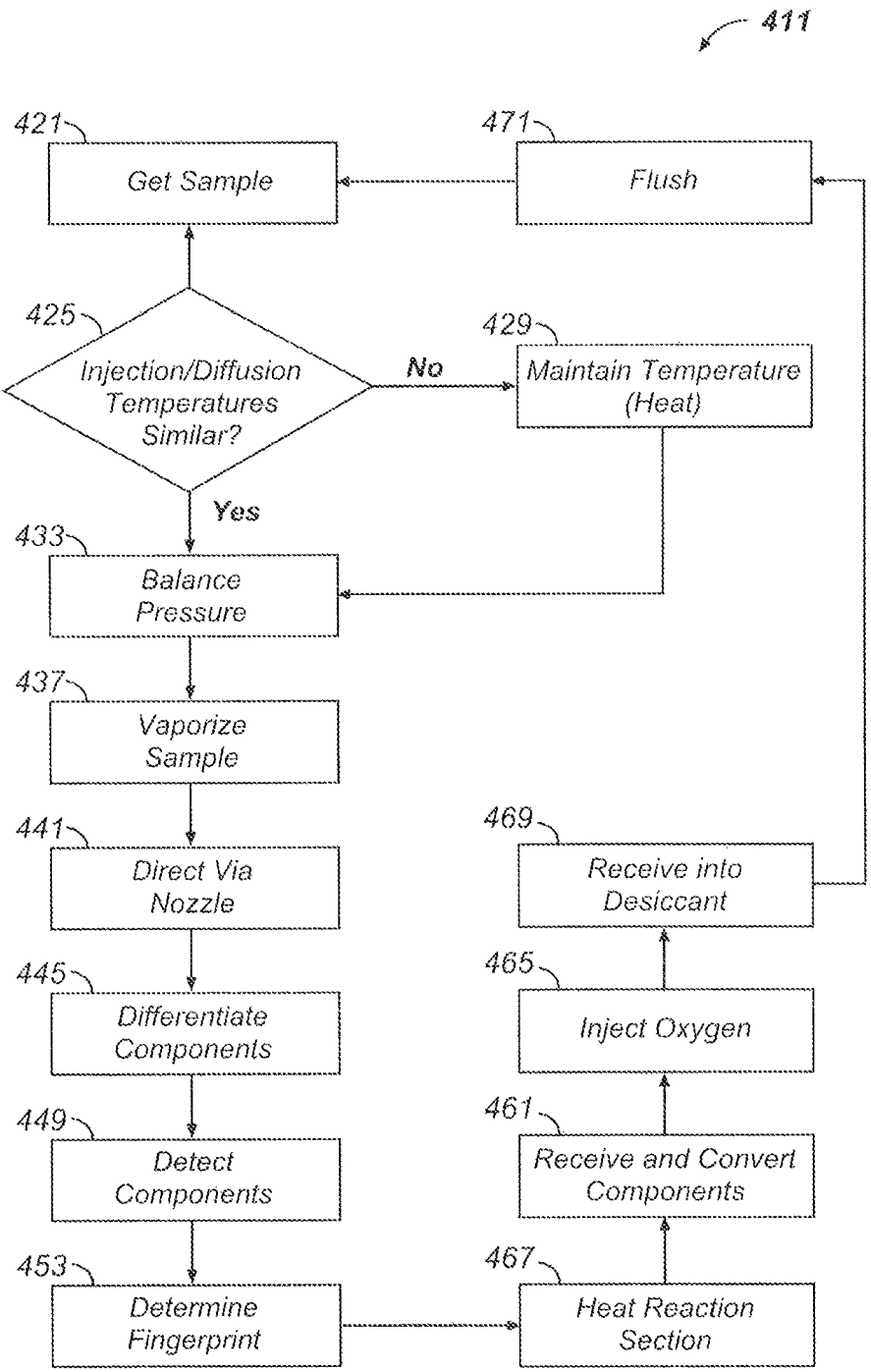
FIG. 4 is a method flow diagram according to various embodiments of the invention.

For example, FIG. 4 is a method flow diagram 411 according to various embodiments of the invention. Thus, a method 411 may begin at block 421 with drawing a formation fluid sample into a sampling port included in a down hole tool. The method 411 may continue on to block 425 with determining whether the temperatures of the injection port and the receiving section are approximately the same. If so, then the method 411 may continue on to block 433.

If the temperatures of the injection port and the receiving section are not approximately the same (e.g., they differ by a predetermined percentage, such as 5%, 10%, or some other amount), then the method 411 may include, at block 429, maintaining the temperature of the injection port and the receiving section at substantially the same value to reduce condensation within at least one of the injection port or the diffusion section. This may be accomplished, for example, by selectively heating the sample port and/or the injection port. Indeed, any and all sections of the apparatus can be heated, if desired, perhaps under computer control.

At block 433, the method may include balancing pressure to reduce mass transport after opening a controllable barrier between the injection port and the receiving section. The receiving section may comprise one or more of a diffusion section, a separation section, or a differentiation section. Pressure balancing can be used to reduce mass transport caused by a pressure gradient across the junction between the injection port and the receiving section.

The method 411 may continue on to block 437 with vaporizing some part of the fluid sample to substantially fill the injection port with a gas phase. The method 411 may further include, at block 441, the activity of directing the gas phase through a nozzle to reduce a pressure gradient at a junction between the injection port and a diffusion section coupled to the injection port.

The method 411 may continue on to block 445 with differentiating gas components in the gas phase to provide differentiated gas components along a concentration gradient. The diffusion section may in some cases be implemented using a membrane, so that differentiating the gas components comprises diffusing the gas phase through the membrane.

The method 411 may continue on to block 449 to include detecting the differentiated gas components. The method 411 may include determining a fingerprint of the differentiated gas components at block 453. Determining the fingerprint may include, in some embodiments, mathematically inverting the differentiated gas components to provide the molecular weight distribution. The activity of mathematically inverting may comprise inverting using any one or more of the following processes: multivariate curve resolution, time evolved factor analysis, or trilinear decomposition, among others.

In some embodiments, the method 411 includes, at block 457, heating a reaction section containing a reactant catalyst comprising a reactive metal oxide. The method 411 may go on to include, at block 461, receiving the differentiated gas components in the reaction section and converting hydrocarbons in the differentiated gas components into at least one of carbon dioxide and water, or oxidized compounds. The reaction section may be included in a negative concentration gradient vacuum section. In some cases, oxidized compounds may arise in a manner similar to or identical to that shown in the equation: $3O_2 + 2H_2S \rightarrow 2SO_2 + 2H_2O$.

In some embodiments, the method 411 may include, at block 465, injecting oxygen into the reaction section to consume at least one of hydrogen, waste, or regenerated catalysts after the differentiated gas components are received in the reaction section. Hydrogen (which can be used as a diffusion medium and flushing medium, and can also be combined with oxygen to make water) and oxygen may be produced by the electrolysis of deionized water. Waste is defined as any substance which poisons the vacuum (e.g., formation fluid components, such as crude oil, $H_2S$, $CO_2$, etc.). Oxygen will react with available materials, such as hydrogen (to make water), waste, or the catalyst—to regenerate the catalyst.

The method 411 may include, at block 469, receiving the differentiated gas components in a desiccant section to absorb products, wherein the desiccant section comprises an oxide. For example, the desiccant section may contain barium oxide.

The method 411 may continue on to block 471 with flushing the receiving section via a capillary tube coupled between the receiving section and a gas reservoir. Flushing the receiving section prior to running another fluid sample permits detection of the existence and quantity of any remainder, which can lead to providing a more complete mass balance between the injection port and the receiving section.

It should be noted that the methods described herein do not have to be executed in the order described. Moreover, various activities described with respect to the methods identified herein can be executed in iterative, serial, or parallel fashion. Information, including parameters, commands, operands, and other data, can be sent and received, and perhaps stored using a variety of media, tangible and intangible, including one or more carrier waves. Any of the activities in these methods may be performed, in part, by a digital electronic system, an analog electronic system, or some combination of the two.

Upon reading and comprehending the content of this disclosure, one of ordinary skill in the art will understand the manner in which a software program can be launched from a computer-readable medium in a computer-based system to execute the functions defined in the software program. One of ordinary skill in the art will further understand that various programming languages may be employed to create one or more software programs designed to implement and perform the methods disclosed herein. The programs may be structured in an object-orientated format using an object-oriented language such as Java or C++. Alternatively, the programs can be structured in a procedure-orientated format using a procedural language, such as assembly, FORTRAN or C. The software components may communicate using any of a number of mechanisms well known to those skilled in the art, such as application program interfaces or interprocess communication techniques, including remote procedure calls. The teachings of various embodiments are not limited to any particular programming language or environment. Thus, other embodiments may be realized.

Articles of Manufacture

Figure 5:
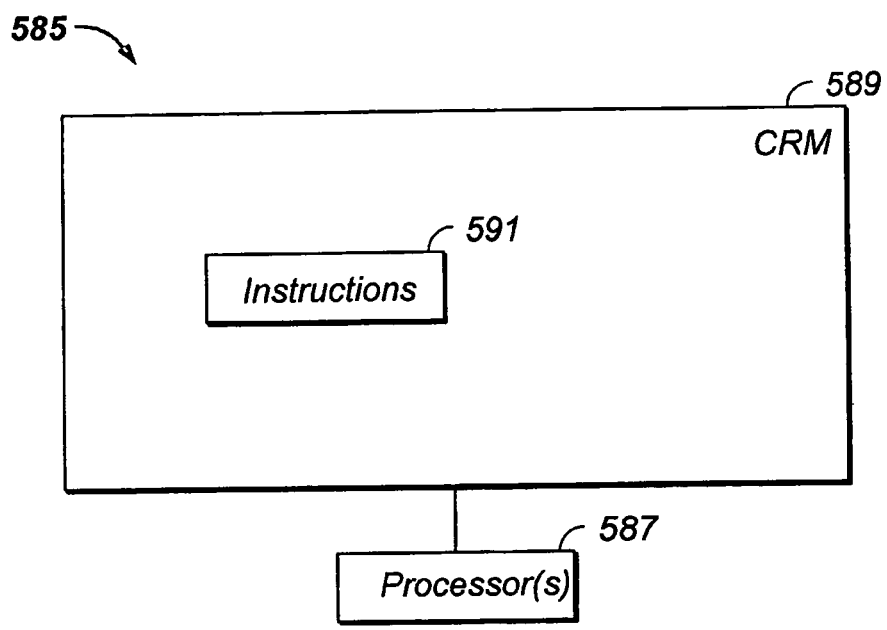
FIG. 5 is a block diagram of an article of manufacture according to various embodiments of the invention.

For example, FIG. 5 is a block diagram of an article 585 according to various embodiments of the invention. The article 585 comprises an article of manufacture, such as a computer, a memory system, a magnetic or optical disk, some other storage device, and/or any type of electronic device or system. For example, the article 585 may include one or more processors 587 coupled to a computer-readable medium 589 such as a memory (e.g., fixed and removable storage media, including tangible memory having electrical, optical, or electromagnetic conductors) having associated information 591 (e.g., computer program instructions and/or data), which when executed by a computer, causes the computer (e.g., the processor(s) 587) to perform a method including such actions as drawing a formation fluid sample into a sampling port included in a down hole tool, vaporizing some part of the fluid sample to substantially fill an injection port with a gas phase, differentiating gas components in the gas phase to provide differentiated gas components along a concentration gradient, detecting the differentiated gas components, and determining a molecular weight distribution of the differentiated gas components.

Additional actions may include, for example, selectively heating the sample port and the injection port, and mathematically inverting the differentiated gas components to provide the molecular weight distribution. Indeed, any of the activities described with respect to the various methods above may be implemented in this manner.

Thus, it should be noted that various embodiments of the invention described herein provide a useful, concrete, and tangible result. The embodiments disclosed are useful because, for example, the fingerprint of a formation fluid sample can directly indicate how easy or difficult petroleum recovery operations may be. This indication is specific, substantial, and credible.

For example, fluid sample fingerprints are concrete, since their determination is substantially repeatable. Fluid sample fingerprints are also tangible, because they convey real-world, as opposed to abstract, information regarding the composition of formation fluids surrounding the borehole at the point where samples are taken.

Conclusion

Implementing the apparatus, systems, and methods of various embodiments may provide the ability to determine formation fluid characteristics in real time, with greater accuracy than was previously achieved. Thus, formation fluid characteristics, and the effect on petroleum recovery operations, may be arrived at with greater confidence in a variety of situations.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A computer-implemented method comprising:
    drawing a formation fluid sample into a sampling port included in a down hole tool;
    vaporizing some part of the fluid sample to substantially fill an injection port with a gas phase;
    differentiating gas components in the gas phase to provide differentiated gas components along a concentration gradient;
    heating a reaction section containing a reactant catalyst comprising a reactive metal oxide;
    receiving the differentiated gas components in the reaction section and converting hydrocarbons in the differentiated gas components into at least one of carbon dioxide and water, or oxidized compounds;
    detecting the differentiated gas components; and
    determining a fingerprint of the differentiated gas components.

2. The method of claim 1, wherein the method includes using a separation section to receive the gas phase from the injection port to provide the differentiated gas components along a concentration gradient.

3. The method of claim 1, wherein the reaction section may be included in a negative concentration gradient vacuum section.

4. The method of claim 1, wherein the oxidized compounds includes sulfur oxide.

5. A computer-implemented method comprising:
    drawing a formation fluid sample into a sampling port included in a down hole tool;
    vaporizing some part of the fluid sample to substantially fill an injection port with a gas phase;
    differentiating gas components in the gas phase to provide differentiated gas components along a concentration gradient;
    injecting oxygen into a reaction section to consume at least one of hydrogen, waste, or regenerated catalysts after receiving the differentiated gas components in the reaction section;
    detecting the differentiated gas components; and
    determining a fingerprint of the differentiated gas components.

6. The method of claim 5, wherein injecting oxygen into the reaction section includes injecting oxygen to directly consume hydrogen without consuming copper oxide that is disposed in the reaction chamber.

7. The method of claim 5, wherein determining the fingerprint includes operating a processor such that the differentiated gas components are inverted to provide the molecular weight distribution in response to detecting the differentiated gas components.

8. The method of claim 7, wherein operating the processor includes inverting using one or more of multivariate curve resolution, time evolved factor analysis, or trilinear decomposition.

9. A computer-implemented method comprising:
    drawing a formation fluid sample into a sampling port included in a down hole tool;
    vaporizing some part of the fluid sample to substantially fill an injection port with a gas phase; differentiating gas components in the gas phase to provide differentiated gas components along a concentration gradient;
    receiving the differentiated gas components in a desiccant section to absorb products, wherein the desiccant section comprises an oxygen containing material;
    detecting the differentiated gas components; and
    determining a fingerprint of the differentiated gas components.

10. The method of claim 9, wherein the oxygen containing material includes barium oxide.

11. The method of claim 9, wherein the oxygen containing material includes an oxide of aluminum, calcium, or magnesium.

12. The method of claim 9, wherein the oxygen containing material includes one or more of magnesium perchlorate, calcium sulfate, copper sulfate, magnesium sulfate, sodium sulfate, boric anhydride, phosphoric acid, phosphorous pentoxide, potassium carbonate, potassium hydroxide, sodium hydroxide, silica gel, or sulfuric acid.

13. A computer-implemented method comprising:
    drawing a formation fluid sample into a sampling port included in a down hole tool;
    vaporizing some part of the fluid sample to substantially fill an injection port with a gas phase;
    directing the gas phase through a nozzle to reduce a pressure gradient at a junction between the injection port and a diffusion section coupled to the injection port;
    differentiating gas components in the gas phase to provide differentiated gas components along a concentration gradient;
    detecting the differentiated gas components; and
    determining a fingerprint of the differentiated gas components.

14. The method of claim 13, wherein the nozzle is arranged to provide an orifice with a pressure differential to prevent back diffusion of gas from a detector section, the detector section arranged for detecting the differentiated gas components.

15. The method of claim 13, wherein the nozzle is arranged to concentrate flow from the diffusion section over a detector, the detector arranged for detecting the differentiated gas components.

16. The method of claim 13, wherein determining the fingerprint includes determining a molecular weight distribution of the differentiated gas components.

17. A computer-implemented method comprising:
drawing a formation fluid sample into a sampling port included in a down hole tool;
vaporizing some part of the fluid sample to substantially fill an injection port with a gas phase;
differentiating gas components in the gas phase to provide differentiated gas components along a concentration gradient, wherein differentiating the gas components includes diffusing the gas phase through a membrane;
detecting the differentiated gas components; and
determining a fingerprint of the differentiated gas components.

18. The method of claim 17, wherein diffusing the gas phase through the membrane includes diffusing the gas phase through the membrane as a function of molecular weight.

19. The method of claim 17, wherein detecting the differentiated gas components includes using one or more of a thermal conductivity detector, a flame ionization detector, a photometric detector, a chip-based mass spectrometer, or an optical detector.

20. The method of claim 17, wherein determining the fingerprint includes operating a processor such that the differentiated gas components are inverted to provide the molecular weight distribution in response to detecting the differentiated gas components.

* * * * *